US011950954B2

(12) United States Patent
Hyun et al.

(10) Patent No.: US 11,950,954 B2
(45) Date of Patent: Apr. 9, 2024

(54) INTRAVASCULAR ULTRASOUND PATIENT INTERFACE MODULE (PIM) FOR DISTRIBUTED WIRELESS INTRALUMINAL IMAGING SYSTEMS

(71) Applicant: KONINKLIJKE PHILIPS N.V., Eindhoven (NL)

(72) Inventors: Nicolas Wonkeun Hyun, Aliso Viejo, CA (US); Hoa Do, San Diego, CA (US); Yannick Marama Kuo, San Diego, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 300 days.

(21) Appl. No.: 16/496,095

(22) PCT Filed: Mar. 5, 2018

(86) PCT No.: PCT/EP2018/055361
§ 371 (c)(1),
(2) Date: Sep. 20, 2019

(87) PCT Pub. No.: WO2018/177690
PCT Pub. Date: Oct. 4, 2018

(65) Prior Publication Data
US 2021/0106307 A1 Apr. 15, 2021

Related U.S. Application Data

(60) Provisional application No. 62/479,152, filed on Mar. 30, 2017.

(51) Int. Cl.
*A61B 8/12* (2006.01)
*A61B 8/00* (2006.01)

(52) U.S. Cl.
CPC ............. *A61B 8/12* (2013.01); *A61B 8/445* (2013.01); *A61B 8/4472* (2013.01); *A61B 8/461* (2013.01); *A61B 8/54* (2013.01); *A61B 8/565* (2013.01)

(58) Field of Classification Search
CPC ......... A61B 8/12; A61B 8/445; A61B 8/4472; A61B 8/461; A61B 8/54; A61B 8/565
See application file for complete search history.

(56) References Cited

U.S. PATENT DOCUMENTS 7,846,101 B2    12/2010   Eberle
9,402,601 B1 *   8/2016   Berger ................. A61B 8/54
(Continued)

FOREIGN PATENT DOCUMENTS

CN     104840217 A     8/2015

OTHER PUBLICATIONS

Paul Lee, "Enabling devices for a Power over Ethernet world," 2015, Murata Power Solutions, pp. 1-4 (Year: 2015).*
(Continued)

*Primary Examiner* — Joseph M Santos Rodriguez
*Assistant Examiner* — Maria Christina Talty

(57) ABSTRACT

An intraluminal imaging system is provided. The intraluminal imaging system includes a patient interface module (PIM) in communication with an intraluminal device comprising an ultrasound imaging component and positioned within a body lumen of a patient, a wireless router via an signal link, and a computing device in wireless communication with the wireless router, wherein the PIM comprises a processing component configured to receive an ultrasound echo signal from the ultrasound imaging component; and determine image data based on at least the ultrasound echo signal; and a power and communication component configured to receive power from the signal link; and transmit, to (Continued)

the computing device via the signal link and the wireless router, the image data.

23 Claims, 6 Drawing Sheets

(56) References Cited

U.S. PATENT DOCUMENTS

| | | |
|---|---|---|
| 2008/0234582 A1 | 9/2008 | Nair |
| 2010/0087782 A1 | 4/2010 | Ghaffari |
| 2014/0039308 A1* | 2/2014 | Blanz .................. A61B 8/12 |
| | | 600/425 |
| 2014/0152467 A1 | 6/2014 | Spencer |
| 2014/0177935 A1 | 6/2014 | Nair |
| 2014/0180032 A1 | 6/2014 | Millett |
| 2014/0180071 A1* | 6/2014 | Stigall ............... A61B 5/6852 |
| | | 600/424 |
| 2014/0180087 A1 | 6/2014 | Millett |
| 2014/0218210 A1* | 8/2014 | De Jong ............. A61B 5/742 |
| | | 340/870.02 |
| 2014/0275844 A1 | 9/2014 | Hoseit |
| 2014/0276017 A1 | 9/2014 | Sproul |
| 2014/0303452 A1 | 10/2014 | Ghaffari |
| 2014/0343434 A1* | 11/2014 | Elbert ................ A61B 8/12 |
| | | 600/467 |
| 2015/0049407 A1 | 2/2015 | Tanimoto |
| 2015/0086098 A1 | 3/2015 | Nair |
| 2015/0087986 A1 | 3/2015 | Nair |
| 2016/0081657 A1 | 3/2016 | Rice |
| 2016/0157803 A1* | 6/2016 | Keller ................ A61B 8/12 |
| | | 600/427 |
| 2016/0166327 A1* | 6/2016 | Keller ................ A61B 5/6876 |
| | | 623/1.1 |
| 2016/0262722 A1* | 9/2016 | Marmor ............. A61B 8/4254 |
| 2016/0302761 A1* | 10/2016 | Lee .................... A61B 8/469 |
| 2016/0302772 A1* | 10/2016 | Cummins ........... A61B 8/54 |
| 2018/0220993 A1* | 8/2018 | Poland ............... G01S 7/5208 |

OTHER PUBLICATIONS

International Search Report & Written Opinion of PCT/EP2018/055361, dated Jun. 15, 2018.

* cited by examiner

INTRAVASCULAR ULTRASOUND PATIENT INTERFACE MODULE (PIM) FOR DISTRIBUTED WIRELESS INTRALUMINAL IMAGING SYSTEMS

TECHNICAL FIELD

The present disclosure relates generally to intraluminal imaging and, in particular, to decoupling image processing and image generation from control and display by generating image data at an intravascular ultrasound (IVUS)-patient interface module (PIM) and distributing the image data wirelessly to multiple diagnostic console and/or control systems via a wireless router.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, and/or to assess its effectiveness. An IVUS device including one or more ultrasound transducers is passed into the vessel and guided to the area to be imaged. The transducers emit ultrasonic energy in order to create an image of the vessel of interest. Ultrasonic waves are partially reflected by discontinuities arising from tissue structures (such as the various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed. IVUS imaging can provide detailed and accurate measurements of lumen and vessel sizes, plaque areas and volumes, and location of key anatomical landmarks. IVUS imaging allows physicians to evaluate the size of a lesion, select a treatment device (e.g., a stent) based on the evaluated lesion size, and subsequently evaluate the treatment success.

There are two types of IVUS catheters commonly in use today: rotational and solid-state. For a typical rotational IVUS catheter, a single ultrasound transducer element is located at the tip of a flexible driveshaft that spins inside a plastic sheath inserted into the vessel of interest. The transducer element is oriented such that the ultrasound beam propagates generally perpendicular to the axis of the device. The fluid-filled sheath protects the vessel tissue from the spinning transducer and driveshaft while permitting ultrasound signals to propagate from the transducer into the tissue and back. As the driveshaft rotates, the transducer is periodically excited with a high voltage pulse to emit a short burst of ultrasound. The same transducer then listens for the returning echoes reflected from various tissue structures. The IVUS imaging system assembles a two dimensional display of the vessel cross-section from a sequence of pulse/acquisition cycles occurring during a single revolution of the transducer.

Solid-state IVUS catheters carry an ultrasound imaging assembly that includes an array of ultrasound transducers distributed around its circumference along with one or more integrated circuit controller chips mounted adjacent to the transducer array. The solid-state IVUS catheters are also referred to as phased array IVUS transducers or phased array IVUS devices. The controllers select individual transducer elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation). Since there is no rotating mechanical element, the transducer array can be placed in direct contact with the blood and vessel tissue with minimal risk of vessel trauma.

In operation, an IVUS device may be connected to a number of cables, for example, a power cable and a communication cable. The IVUS device may receive power from the power cable for operating an ultrasound imaging assembly included in the IVUS device. The IVUS device may communicate with a console or processing system over the communication cable for controlling the operations of the ultrasound imaging assembly and reading out measurements (e.g., ultrasound echo signals) collected by the ultrasound imaging assembly, analyzing and processing the images for display.

IVUS procedures are typically performed in a catheter lab. The use of the IVUS device in the catheter lab increases the number of cables in the catheter lab and may clutter the workspace of the catheter lab. In some instances, it may be desirable to output image data to multiple diagnostic systems for various aspects of a workflow, which further increasing the amount of cabling. These conditions can make a physician's ability to gather medical images and/or data for patient diagnosis more challenging.

SUMMARY

While existing intraluminal imaging systems have proved useful, there remains a need for improved systems and techniques for reducing the amount of cabling between intraluminal imaging devices and systems in catheter labs. Embodiments of the present disclosure provide an IVUS-PIM that determines image data based on ultrasound echo signals collected from an ultrasound imaging component and distributes the image data wirelessly to multiple systems via a power over Ethernet (PoE) connection to a wireless router. For example, the IVUS-PIM is coupled to an intraluminal imaging device including an ultrasound imaging component and a wireless router via an Ethernet cable. The IVUS-PIM includes a processing component coupled to the ultrasound imaging component and a PoE component coupled to the Ethernet cable. The PoE component receives power from the Ethernet cable to power the IVUS-PIM and the intraluminal imaging device. During a medical procedure, the intraluminal imaging device can be inserted into a vessel of a patient and the ultrasound imaging component can emit ultrasound signals and receive ultrasound echo signal reflected from the structure of the vessel. The processing component receives the ultrasound echo signals and applies imaging algorithms to determine image data from the received ultrasound echo signals. The processing component formats the image data into a suitable image display format. The PoE component transmits and distributes the image data to one or more diagnostic systems that are in wireless communication with the wireless router. The PoE component can also receive control and/or data signals from one or more diagnostic systems for imaging and image processing and generation.

In one embodiment, an intraluminal imaging system is provided. The intraluminal imaging system includes a patient interface module (PIM) in communication with an intraluminal device comprising an ultrasound imaging component and positioned within a body lumen of a patient, a wireless router via a signal link, and a computing device in wireless communication with the wireless router, wherein the PIM comprises a processing component configured to receive an ultrasound echo signal from the ultrasound imaging component; and determine image data based on at least the ultrasound echo signal; and a power and communication component configured to receive power from the signal link; and transmit, to the computing device via the signal link and the wireless router, the image data.

In some embodiments, the power and communication component is further configured to receive a control signal from the computing device via the signal link and the wireless router, and wherein the processing component is further configured to receive the ultrasound echo signal based on at least the control signal. In some embodiments, the power and communication component is further configured to receive a control signal from the computing device via the signal link and the wireless router, wherein the processing component is further configured to transmit an ultrasound signal transmission trigger to the ultrasound imaging component based on at least the control signal, and wherein the ultrasound echo signal is associated with the ultrasound signal transmission trigger. In some embodiments, the power and communication component is further configured to receive a control signal from the computing device via the signal link and the wireless router, and wherein the processing component is further configured to determine the image data based on the control signal. In some embodiments, the power and communication component is further configured to provide the power received from the signal link to the ultrasound imaging component of the intraluminal device. In some embodiments, the power and communication component is further configured to provide the power received from the signal link to the processing component. In some embodiments, the PIM further includes a memory coupled to the processing component and configured to store the image data. In some embodiments, the power and communication component is further configured to receive, from a medical diagnostic system via the signal link and the wireless router, an image border line, and wherein the processing component is further configured to determine the image data further according to the image border line. In some embodiments, the intraluminal system further comprises the intraluminal device. In some embodiments, the ultrasound imaging component comprises one or more ultrasound transducers. In some embodiments, the PIM further comprises a patient isolation circuit coupled between the power and communication component and the processing component. In some embodiments, the processing component is further configured to format the image data according to an image display format usable by the computing device to display the image data, and wherein the power and communication component is further configured to transmit the image data by transmitting the image data in the image display format usable by the computing device to display the image data. In some embodiments, the PIM is in communication with a second computing device in wireless communication with the wireless router, and wherein the power and communication component is further configured to transmit, to the second computing device via the signal link and the wireless router, the image data.

In one embodiment, a method of performing intraluminal imaging includes receiving, by a patient interface module (PIM) from an intraluminal imaging device, an ultrasound echo signal associated with a body lumen of a patient; determining, by the PIM, image data based on at least the ultrasound echo signal; receiving, by the PIM, power from a wireless router via a signal link; and transmitting, by the PIM to a computing device via the signal link and the wireless router, the image data.

In some embodiments, the method further includes receiving, by the PIM from the computing device via the signal link and the wireless router, a control signal, wherein the receiving the ultrasound echo signal includes receiving the ultrasound echo signal based on at least the control signal. In some embodiments, the method further includes receiving, by the PIM from the computing device via the signal link and the wireless router, a control signal; and transmitting, by the PIM to the intraluminal imaging device, an ultrasound signal transmission trigger based on at least the control signal, wherein the ultrasound echo signal is associated with the ultrasound signal transmission trigger. In some embodiments, the method further includes receiving, by the PIM from the computing device via the signal link and the wireless router, a control signal, wherein the determining the image data includes determining the image data further based on at least the control signal. In some embodiments, the method further includes receiving, by the PIM from a medical diagnostic system via the signal link and the wireless router, an image border line, wherein the determining the image data includes determining the image data according to the image border line. In some embodiments, the method further includes formatting, by the PIM, the image data according to an image display format of the computing device, wherein the transmitting the image data includes transmitting the image data in the image display format of the computing device. In some embodiments, the method further includes transmitting, by the PIM to a second computing device via the signal link and the wireless router, the image data.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
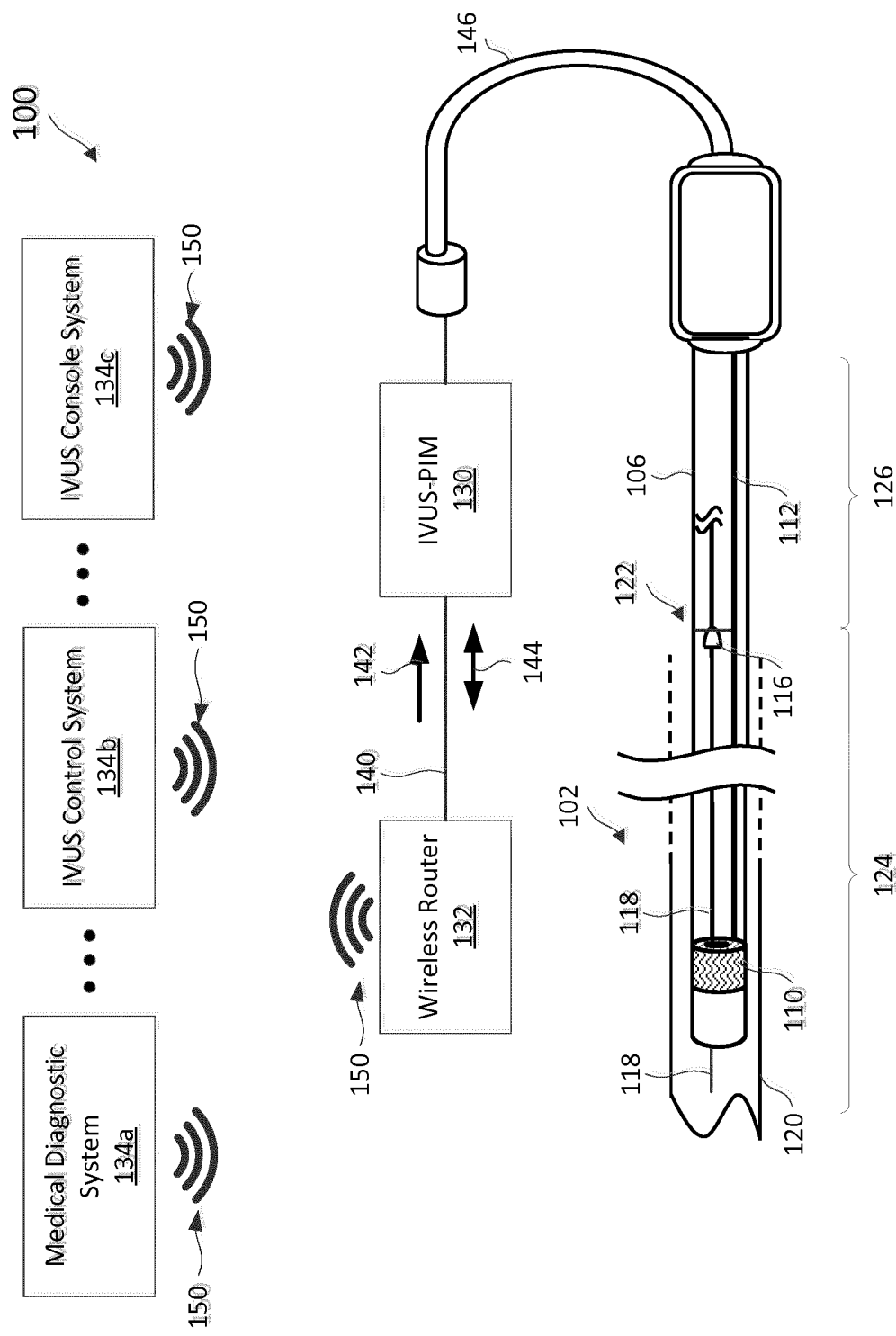
FIG. 1 is a schematic diagram of a distributed wireless intraluminal imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of a distributed wireless intraluminal imaging system 100, according to aspects of the present disclosure. The system 100 may include an IVUS device 102, an IVUS-PIM 130, a wireless router 132, a plurality of distributed systems 134, for example, including a medical diagnostic system 134a, an IVUS control system 134b, and an IVUS console system 134c. The IVUS-PIM 130 is in communication with the IVUS device 102 and the wireless router 132. The IVUS-PIM 130 is connected to the wireless router 132 via an Ethernet cable 140. The Ethernet cable 140 functions as a signal link or PoE link delivering power to the IVUS-PIM 130 and the IVUS device 102 as shown by the arrow 142 and transporting data between the IVUS-PIM 130 and the wireless router 132 as shown by the arrow 144. The wireless router 132 is in wireless communication with the systems 134 as shown by the radio frequency (RF) signals 150. Thus, the IVUS-PIM 130 can communicate with one or more of the systems 134 via the wireless router 132.

The IVUS device 102 may include a flexible elongate member 106, which may be a catheter, a guide wire, or a guide catheter. The IVUS device 102 may further include an ultrasound imaging assembly 110. The ultrasound imaging assembly 110 may be mounted at a distal portion 124 near a distal end of the flexible elongate member 106.

The IVUS-PIM 130 is coupled to a proximal end of the flexible elongate member 106. The IVUS device 102 further includes an electrical cable 112 extending along the flexible elongate member 106 between the ultrasound imaging assembly 110 and the IVUS-PIM 130. The electrical cable 112 may carry control signals, echo data, and/or power between the IVUS-PIM 130 and the IVUS device 102.

At a high level, the IVUS device 102 can be inserted into a vessel 120 of a patient. The IVUS device 102 emits ultrasonic energy from a transducer array included in the ultrasound imaging assembly 110. The ultrasonic energy is reflected by tissue structures of the vessel 120 surrounding the ultrasound imaging assembly 110, and the ultrasound echo signals are received by the transducer array in the ultrasound imaging assembly 110. The electrical cable 112 transfers the ultrasound echo signals to the IVUS-PIM 130.

The vessel 120 may represent fluid filled or surrounded structures, both natural and man-made. The vessel 120 may be within a body of a patient. The vessel 120 may be a blood vessel, as an artery or a vein of a patient's vascular system, including cardiac vasculature, peripheral vasculature, neural vasculature, renal vasculature, and/or or any other suitable lumen inside the body. For example, the IVUS device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the IVUS device 102 may be used to examine man-made structures such as, but without limitation, heart valves, stents, shunts, filters and other devices.

The IVUS-PIM 130 includes a processing component (a processing component 410 shown in FIGS. 4 and 5), which may include hardware and/or software, configured to determine image data based on the ultrasound echo signals, for example, by applying image processing algorithms and/or image analytic algorithms to the ultrasound echo signals. For example, the IVUS-PIM 130 can generate image data for a cross-sectional view of the vessel 120.

In an embodiment, the IVUS device 102 further includes a guide wire exit port 116 disposed near a junction 122 at which a distal portion 124 is coupled to a proximal portion 126. Accordingly, in some instances the IVUS device 102 is a rapid-exchange catheter. The guide wire exit port 116 allows a guide wire 118 to be inserted towards the distal end in order to direct the IVUS device 102 through the vessel 120.

The IVUS-PIM 130 further includes a power and communication component (a PoE component 430 shown in FIG. 4) coupled to the wireless router 132 by the Ethernet cable 140. The wireless router 132 functions as a power sourcing equipment and the IVUS-PIM 130 function as a power device. For example, the power and communication component of the IVUS-PIM 130 draws power from the wireless router 132 and provides the power to the ultrasound imaging assembly 110 over the electrical cable 112. Electrical signals can be transmitted between the IVUS-PIM 130 and the IVUS device 102 via a cable 146.

The Ethernet cable 140 includes multiple twisted pairs. The Ethernet cable 140 can transport power and data over different twisted pairs or the same twisted pairs as described in Institute of Electrical and Electronics Engineers (IEEE) 802.3 standards. The internal components of the IVUS-PIM 130 are described in greater detail herein with respect to FIGS. 4 and 5. The IVUS-PIM 130 communicates the image data to the wireless router 132 via the Ethernet cable 140.

The wireless router 132 may be any wireless communication device or access point configured with support for transporting data and power (e.g., PoE support). The wireless router 132 may include transceivers and antennas configured to communicate with the systems 134 according to any suitable wireless communication protocols, such as IEEE 802.11 (WiFi) standards, fifth generation (5G) wireless communication protocols, or any advanced wireless communication protocol. For example, the wireless router 132 may forward signals received from the systems 134 to the IVUS-PIM 130. In a reverse direction, the wireless router 132 may forward signals received from the IVUS-PIM 130 to the systems 134. The wireless router 132 may include a power and communication component configured to deliver power to the IVUS-PIM 130 and to transport data via the Ethernet cable 140, for example, according to the IEEE 802.3 standards.

The systems 134 may include computing devices including hardware and/or software, consoles, keyboards, display monitors, and/or touchscreens for controlling and/or monitoring physiologic assessments and measurements. The systems 134 may further include wireless communication devices including transceivers and antennas for wireless communication with the wireless router 132. The wireless communication devices may implement a similar wireless communication protocol as the wireless router 132 for communication with the wireless router 132. Thus, in some embodiments, the systems 134 may be wireless computer workstations, wireless tablets, and/or any mobile devices.

The IVUS control system 134b can send control signals carrying commands for performing medical imaging using the IVUS device 102 and the wireless router 132 can forward the control signals to the IVUS-PIM 130. For example, the IVUS control system 134b may function similar to a bedside controller. The IVUS-PIM 130 can control the ultrasound imaging assembly 110 and/or generate image data according to the control commands. For example, during a medical imaging procedure, a clinician may operate the IVUS control system 134b by sending a start command to begin imaging and generate image data, a recording command to record generated image data, a stop command to stop the acquisition, and/or sending ultrasound signal transmission and/or reception triggers to obtain certain imaging views.

The IVUS-PIM 130 may send the generated image data to the IVUS control system 134b for display via the Ethernet cable 140 and the wireless router 132. In some embodiments, the IVUS-PIM 130 may simultaneously send the generated image data to the IVUS control system 134b, the IVUS console system 134c, and/or the medical diagnostic system 134a for display via the wireless router 132. In some embodiments, the IVUS console system 134c may function as another controller performing different aspects of the workflow than the IVUS control system 134b.

The medical diagnostic system 134a can perform medical measurements and analysis and facilitate medical imaging. For example, the medical system 134a may include instruments or may communicate with instruments performing optical coherence tomography (OCT), electrophysiology (EP) mapping, pressure measurements, flow measurements, and/or electrocardiography (ECG) measurements. The medical diagnostic system 134a can display image data generated by the IVUS-PIM 130 in conjunction with the other medical measurements. The medical diagnostic system 134a may include user interfaces to enable physicians to request other imaging views and/or further computations based on initial image data generated by the IVUS-PIM 130. The medical diagnostic system 134a may send further requests and/or controls to the IVUS-PIM 130 via the wireless router 132, as described in greater detail herein.

The system 100 may use any of a variety of ultrasonic imaging technologies. Accordingly, in some embodiments of the present disclosure, the system 100 is a solid-state IVUS imaging system incorporating an array of piezoelectric transducers fabricated from lead-zirconate-titanate (PZT) ceramic. In some embodiments, the system 100 incorporates capacitive micromachined ultrasonic transducers (CMUTs), or piezoelectric micromachined ultrasound transducers (PMUTs).

In some embodiments, the system 100 includes some features similar to s solid-state IVUS system, such as the EagleEye® catheter available from Volcano Corporation and those disclosed in U.S. Pat. No. 7,846,101 hereby incorporated by reference in its entirety. For example, the IVUS device 102 includes the ultrasound imaging assembly 110 near a distal end of the IVUS device 102 and an electrical cable 112 extending along the longitudinal body of the IVUS device 102. The cable 112 is a transmission line bundle including a plurality of conductors. It is understood that any suitable gauge wire can be used for the conductors 218. In an embodiment, the cable 112 can include a four-conductor transmission line arrangement with, e.g., 41 American wire gauge (AWG) wires. In some embodiments, the system 100 can include features similar a rotational IVUS system, such as the Revolution® catheter available from Volcano Corporation and features disclosed in U.S. Pat. Nos. 5,601,082 and 6,381,350.

Figure 2:
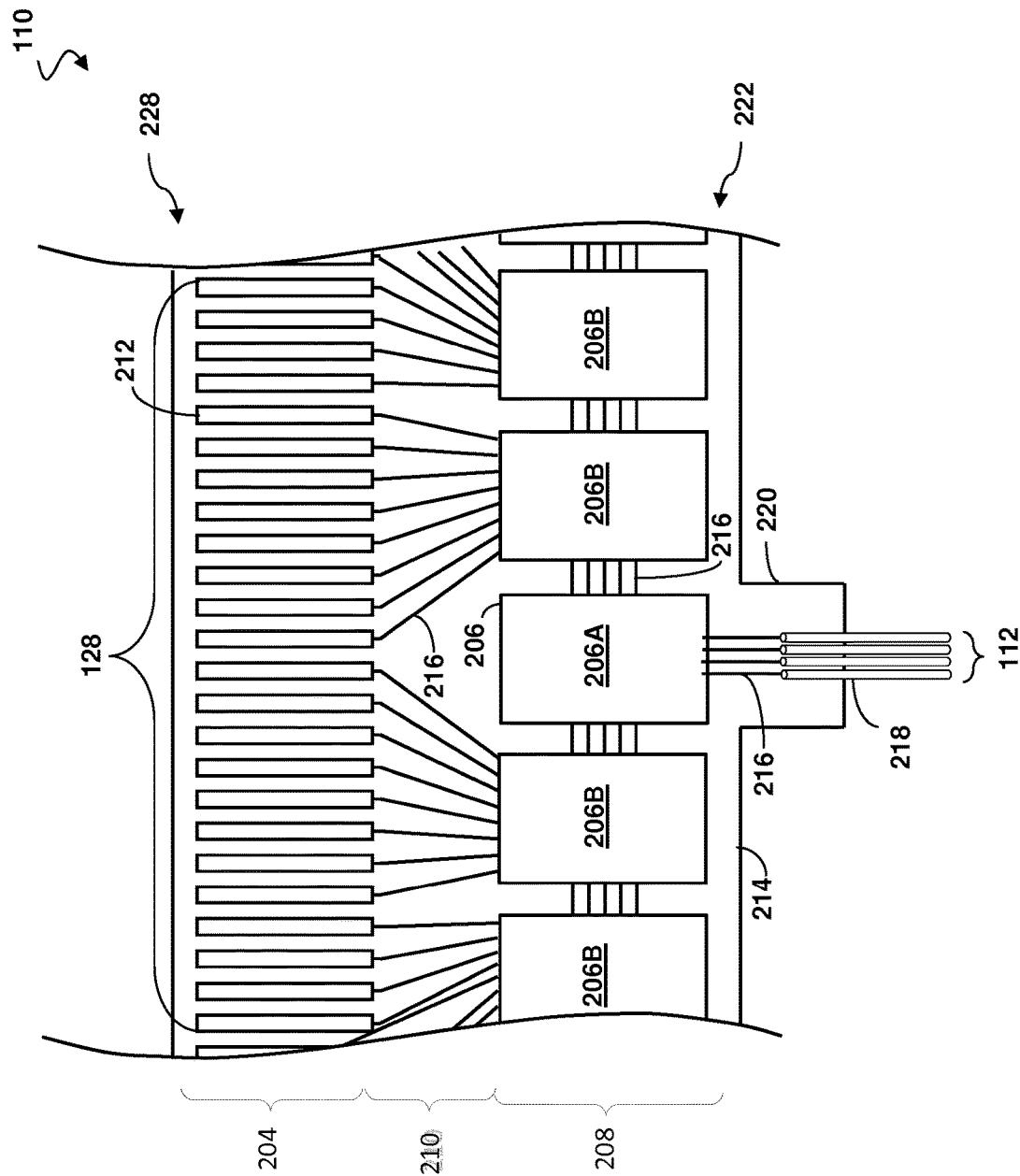
FIG. 2 is a top view of a portion of an ultrasound imaging assembly, according to aspects of the present disclosure.

FIG. 2 is a top view of a portion of the solid state or phased array ultrasound imaging assembly 110, according to aspects of the present disclosure. While FIG. 2 describes a solid state or phased array IVUS imaging assembly, it is understand that features of the present disclosure can be implemented with a rotational IVUS imaging assembly. FIG. 2 illustrates the ultrasound imaging assembly 110 in a flat configuration. The ultrasound imaging assembly 110 includes the transducer array 128 formed in a transducer region 204 and transducer control logic dies 206 (including dies 206A and 206B) formed in a control region 208, with a transition region 210 disposed therein between. The transducer array 128 includes an array of transducers 212. The transducer control logic dies 206 and the transducers 212 are mounted on a flex circuit 214 in a flat form prior to assembling into a final rolled form as shown in FIG. 1. The transducer array 128 is a non-limiting example of a medical sensor element and/or a medical sensor element array. The transducer control logic dies 206 is a non-limiting example of a control circuit. While the ultrasound imaging assembly 110 is described as including a flex circuit, it is understood that the transducers and/or controllers may be arranged to form the ultrasound imaging assembly 110 in other configurations, including those omitting a flex circuit.

The transducer array 128 can include any number and type of ultrasound transducers 212, although for clarity only a limited number of ultrasound transducers are illustrated in FIG. 2. In an embodiment, the transducer array 128 includes 32 individual ultrasound transducers 212. In another embodiment, the transducer array 128 includes 64 ultrasound transducers 212. In another embodiment, the transducer array 128 includes 96 ultrasound transducers 212. In yet another embodiment, the transducer array 128 includes 128 ultrasound transducers 212. Other numbers are both contemplated and provided for. With respect to the types of transducers, in an embodiment, the ultrasound transducers 212 are piezoelectric micromachined ultrasound transducers (PMUTs) fabricated on a micro electromechanical system (MEMS) substrate using a polymer piezoelectric material, for example as disclosed in U.S. Pat. No. 6,641,540, which is hereby incorporated by reference in its entirety. In alternate embodiments, the transducer array 128 includes PZT transducers such as bulk PZT transducers, capacitive micromachined ultrasound transducers (cMUTs), single crystal piezoelectric materials, other suitable ultrasound transmitters and receivers, and/or combinations thereof. While FIG. 2 illustrates the ultrasound transducers 212 arranged in a single row, for example, for two-dimensional (2D) imaging, in some embodiments, the ultrasound transducers 212 can be alternatively arranged in multiple rows forming a matrix of ultrasound transducers 212, for example, for three-dimensional (3D) imaging.

The ultrasound imaging assembly 110 may include various transducer control logic, which in the illustrated embodiment is divided into discrete control logic dies 206. In various examples, the control logic of the ultrasound imaging assembly 110 performs: decoding control signals sent by the NUS-PIM 130 across the cable 112, driving one or more transducers 212 to emit an ultrasonic signal, selecting one or more transducers 212 to receive a reflected echo of the ultrasonic signal, amplifying a signal representing the received echo, and/or transmitting the signal to the IVUS-PIM 130 across the cable 112. In some embodiments, when the transducer array 128 includes cMUTs, the control logic may further include biasing circuitries to optimize the cMUTs for transmit and/or receive. In the illustrated embodiment, an ultrasound imaging assembly 110 having 64 ultrasound transducers 212 divides the control logic across nine control logic dies 206, of which five are shown in FIG. 2. Designs incorporating other numbers of control logic dies 206 including 8, 9, 16, 17 and more are utilized in other embodiments. In general, the control logic dies 206 are characterized by the number of transducers they are capable of driving, and exemplary control logic dies 206 drive 4, 8, and/or 16 transducers.

The control logic dies 206 are not necessarily homogenous. In some embodiments, a single controller is designated a master control logic die 206A and contains the communication interface for the cable 112. Accordingly, the master control circuit may include control logic that decodes control signals received over the cable 112, transmits control responses over the cable 112, amplifies echo signals, and/or transmits the echo signals over the cable 112. The remaining controllers are slave controllers 206B. The slave controllers 206B may include control logic that drives a transducer 212 to emit an ultrasonic signal and selects a transducer 212 to receive an echo. In the depicted embodiment, the master controller 206A does not directly control any transducers 212. In other embodiments, the master controller 206A drives the same number of transducers 212 as the slave controllers 206B or drives a reduced set of transducers 212 as compared to the slave controllers 206B. In an exemplary embodiment, a single master controller 206A and eight slave controllers 206B are provided with eight transducers assigned to each slave controller 206B.

To electrically interconnect the control logic dies 206 and the transducers 212, in an embodiment, the flex circuit 214 further includes conductive traces 216 that carry signals between the control logic dies 206 and the transducers 212. In particular, the conductive traces 216 providing communication between the control logic dies 206 and the transducers 212 extend along the flex circuit 214 within a transition region 210 between the transducer region 204 and the control region 208. In some instances, the conductive traces 216 can also facilitate electrical communication between the master controller 206A and the slave controllers 206B. The conductive traces 216 can also provide a set of conductive pads that contact the conductors 218 of cable 112 when the conductors 218 of the cable 112 are mechanically and electrically coupled to the flex circuit 214.

Figure 3:
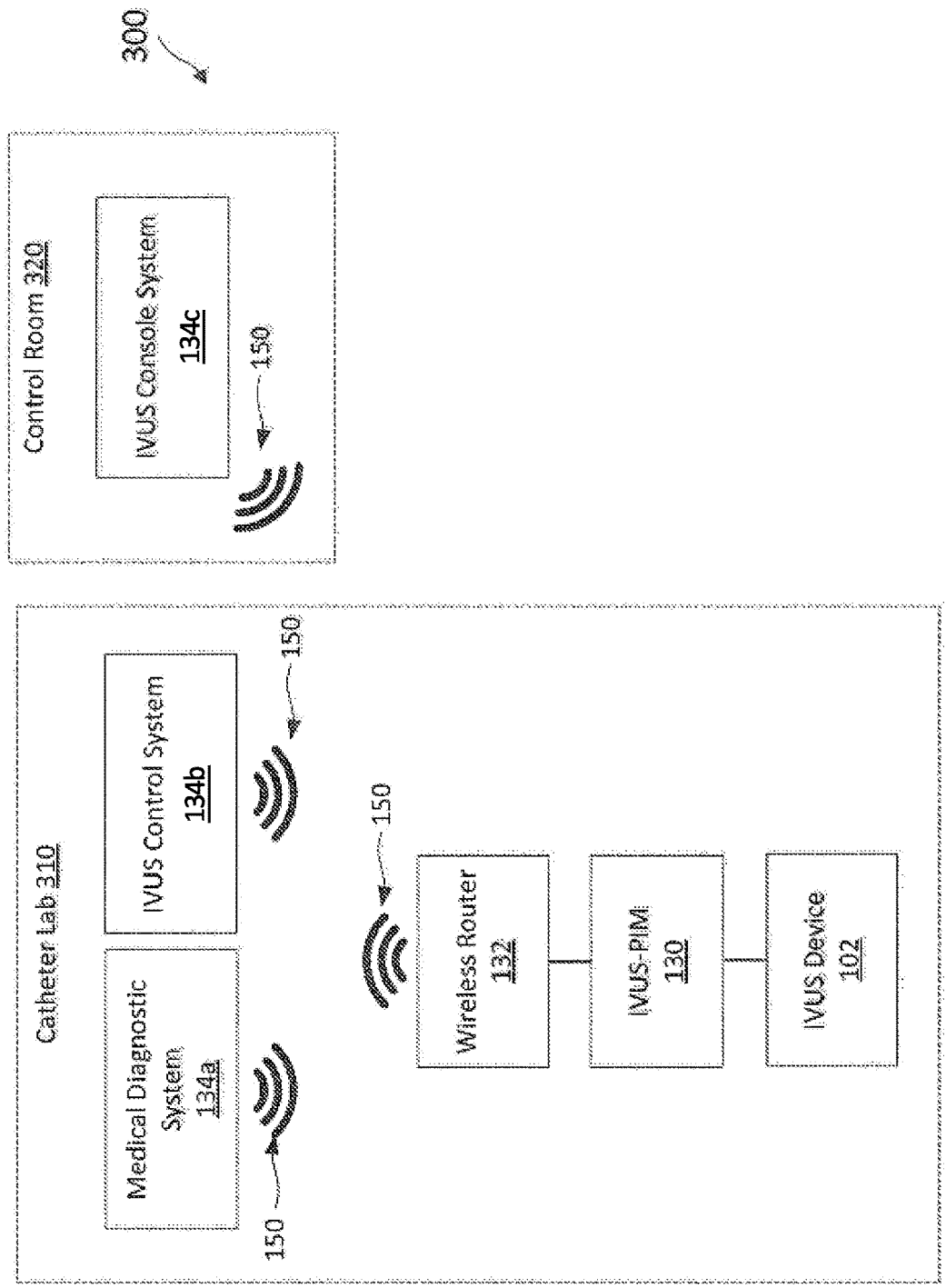
FIG. 3 illustrates a use case scenario for a distributed wireless intraluminal imaging system, according to aspects of the present disclosure.

FIG. 3 illustrates a use case scenario 300 for the distributed wireless intraluminal imaging system 100, according to aspects of the present disclosure. The scenario 300 includes a catheter lab 310 and a control room 320. The catheter lab 310 is an examination room in a hospital or clinic where a physician or a clinician may perform a medical treatment or diagnostic procedure on a patient, for example, using the IVUS device 102. The control room 320 may be another room in the hospital or clinic where anther physician or clinician may monitor the image data obtained from the medical procedure during the procedure. For example, the IVUS device 102, the IVUS-PIM 130, the wireless router 132, the medical diagnostic system 134a, and the IVUS control system 134b are located in the catheter lab 310, while the IVUS console system 134c is located in the control room 320.

During a medical procedure, a physician may insert the IVUS device 102 into a patient vessel (e.g., the vessel 120) of interest. The physician may normalize and/or calibrate the IVUS device 102 by operating the IVUS control system 134b and/or the medical diagnostic system 134a prior to the insertion. The physician may operate the IVUS control system 134b for performing the medical procedure. For example, the physician may start, record, and/or stop image data acquisition. The physician may press a start button, for example, via a graphical user interface (GUI) display on the IVUS control system 134, to begin image data acquisition. The IVUS control system 134 sends a control signal carrying a start command to the wireless router 132. The wireless router 132 forwards the control signal to the IVUS-PIM 130. The IVUS-PIM 130 begins to collect ultrasound echo signals from the ultrasound imaging assembly 110 on the IVUS device 102. The IVUS-PIM 130 computes image data according to the received ultrasound echo signals. The IVUS-PIM 130 transmits the image data to the IVUS control system 134b, the medical diagnostic system 134a, and/or the IVUS console system 134c for display. The physician may also initiate recording and/or stopping the image data acquisition using similar mechanisms as the starting of the data acquisition.

In some embodiments, the medical diagnostic system 134a may facilitate image generation at the IVUS-PIM 130. As described above, the medical diagnostic system 134a can include instruments or communicate with instruments operating in other medical diagnostic modalities. For example, a physician operating the medical diagnostic system 134a can collect images and/or medical data from the instruments as well as images from the IVUS-PIM 130. The physician may determine that more detailed images and/or images of certain areas are required. Thus, the physician may request additional images or images at different resolutions and/or different depths and/or provide additional data to the IVUS-PIM 130 for image generation via the medical diagnostic system 134a, for example, via a GUI on the medical diagnostic system 134a. In an embodiment, a physician may select a border surrounding an area or a structure of interest based on the received images. The medical diagnostic system 134a may send a data signal including the selected border to the IVUS-PIM 130. Upon receiving the data signal, the IVUS-PIM 130 may re-compute image data according to the selected border and/or requests the IVUS device 102 to collect additional ultrasound echo signals for image generation.

Figure 4:
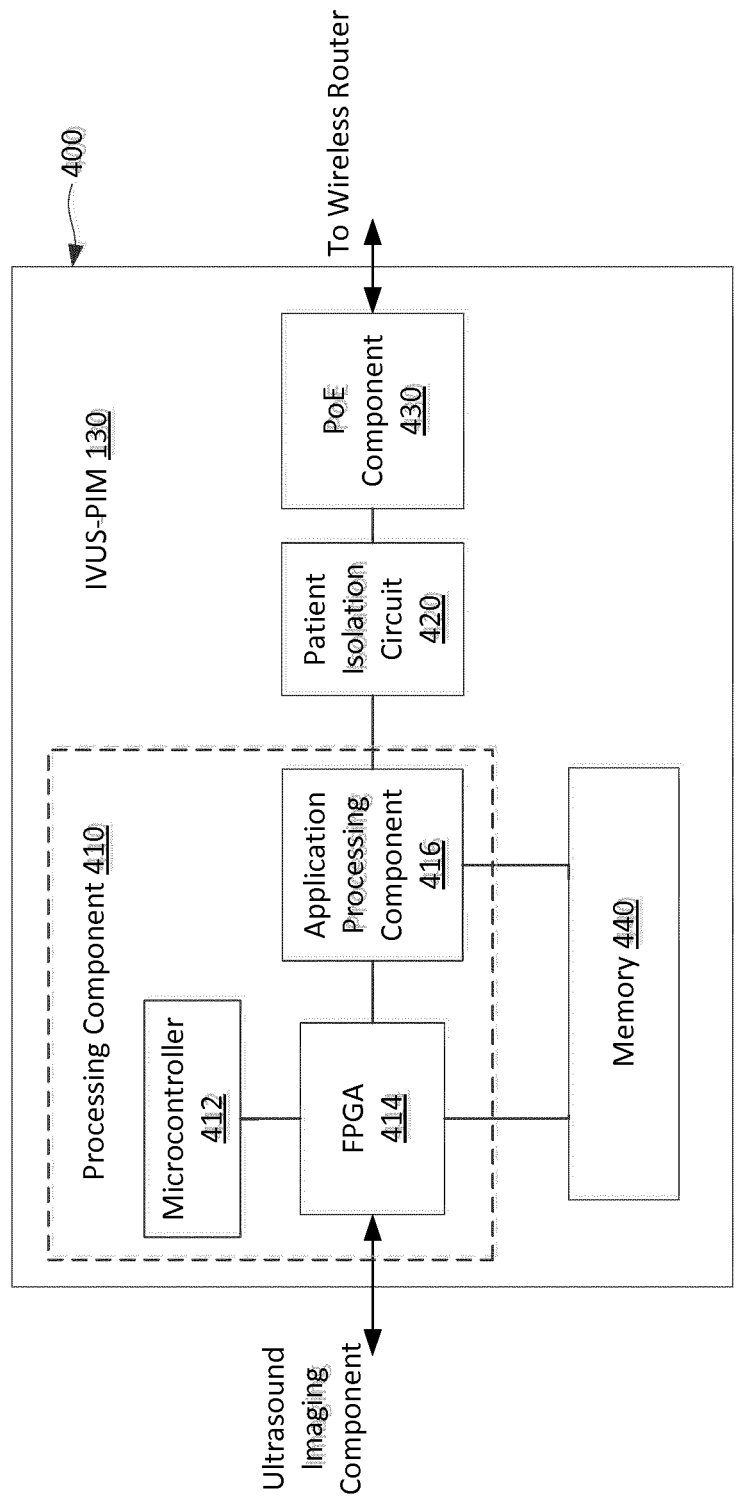
FIG. 4 is a schematic diagram illustrating an architecture of an IVUS-patient interface module (PIM), according to aspects of the present disclosure.
Figure 5:
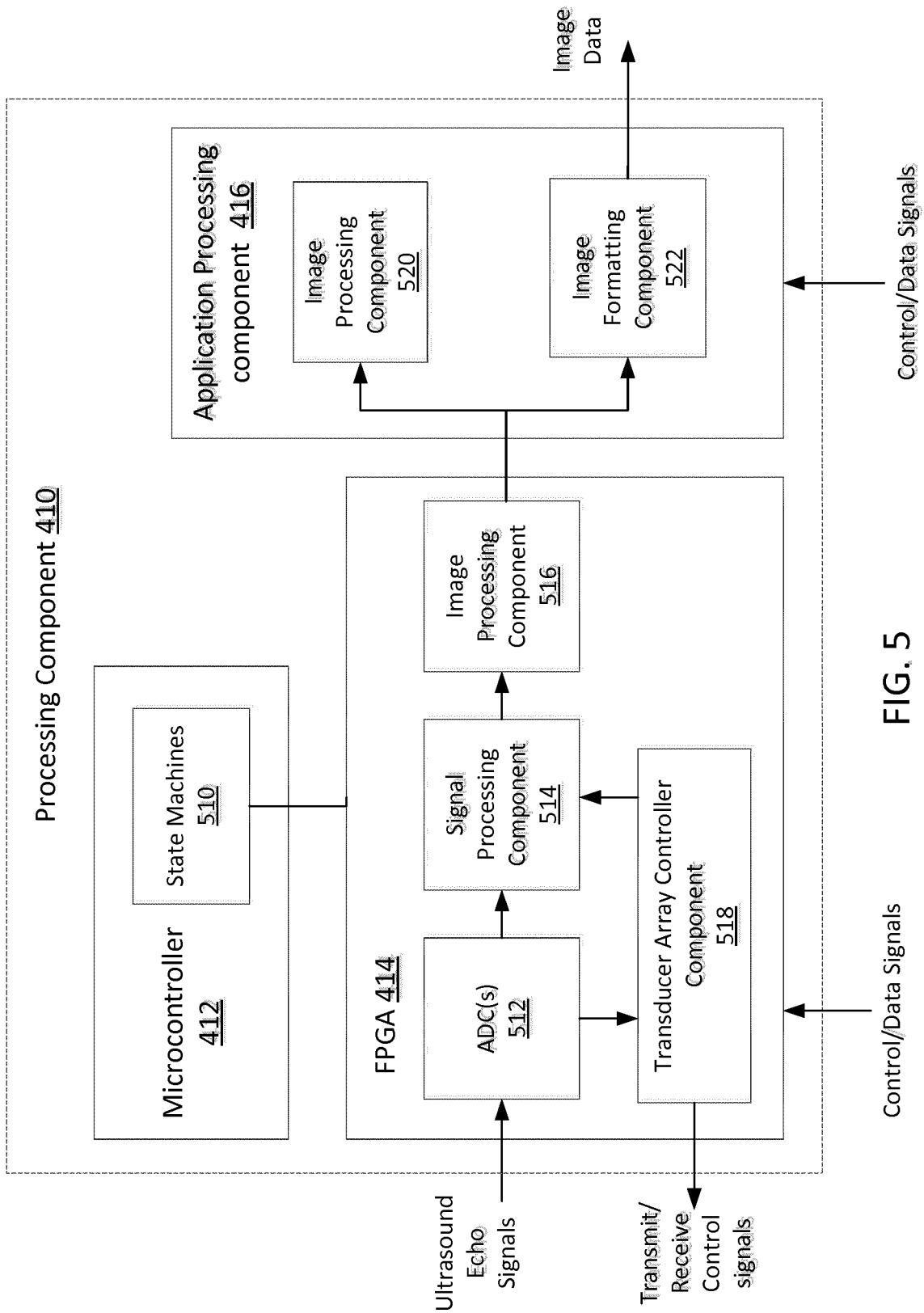
FIG. 5 is a schematic diagram illustrating functional blocks of an IVUS-PIM, according to aspects of the present disclosure.

FIG. 4 is a schematic diagram illustrating an architecture of the IVUS-PIM 130, according to aspects of the present disclosure. FIG. 5 is a schematic diagram illustrating functional blocks of the IVUS-PIM 130, according to aspects of the present disclosure. The IVUS-PIM 130 includes a processing component 410, a patient isolation circuit 420, a PoE component 430, and a memory 440 encased in a housing 400. The housing 400 may be constructed from a rigid material, such as plastic and/or metal. The processing component 410 is coupled to the memory 440, and the ultrasound imaging assembly 110 of the IVUS device 102. The processing component 410 includes a microcontroller 412, a field programmable gate array (FPGA) 414, and an application processing component 416. The patient isolation circuit 420 couples the PoE component 430 to the processing component 410.

The PoE component 430 is a power and communication component configured to draw power and communicate data via the Ethernet cable 140. For example, the PoE component 430 may include a PoE controller, an Ethernet device, a direct current (DC)/DC converter. The PoE controller draws or requests power from the wireless router 132 via the Ethernet cable 140. The PoE device controller may also handle signaling required for PoE communication. The DC/DC converter converts input voltage received from the wireless router 132 into a suitable voltage level for operating the processing component 410 and the ultrasound imaging assembly 110. For example, the PoE component 430 is coupled to the power circuitry within the IVUS-PIM 130 and the electrical cable 112 of the IVUS device 102. The Ethernet device may include transceivers and medium access control (MAC) processors configured to communicate data with the wireless router 132 according to an Ethernet protocol. The transportations of the data and power may be over the same twisted pair or different twisted pairs.

The patient isolation circuit 420 includes circuitry configured to provide electrical isolation between the PoE component 430 and the IVUS device 102, which is in contact with a patient body when in use. For example, in an event where a short or electrical malfunction occurs, the patient isolation circuit 420 may restrict the line voltage from passing from the PoE component 430 to the patient undergoing an intraluminal imaging procedure. The patient isolation circuit 420 may also restrict the amount of low-level RF signals that may be passed to the patient body.

The memory 440 may include volatile memory and non-volatile memory of any suitable memory types, including random access memory (RAM), read-only memory (ROM), programmable read-only memory (PROM), erasable programmable read-only memory (EPROM), electrically erasable programmable read-only memory (EEPROM), dynamic random-access memory (DRAM), static random-access memory (SRAM), and combinations thereof. The memory 440 is configured to store image data generated by the processing component 410.

As shown in FIG. 5, the FPGA 414 includes one or more analog-to-digital converters (ADCs) 512, a signal processing component 514, an image processing component 516, and a transducer array controller component 518. The ADCs 512 includes circuitry configured to receive analog ultrasound echo signals from the ultrasound imaging component (e.g., the transducer array 128) on the ultrasound imaging assembly 110 and convert the analog ultrasound echo signals into digital signals. The signal processing component 514 is coupled to the ADCs 512. The signal processing component 514 is configured to perform signal conditioning on the digital signals. Signal conditioning may include amplification, filtering, and quadrature demodulation.

The transducer array controller component 518 is coupled to the ultrasound imaging assembly 110, the ADCs 512, and the signal processing component 514. The transducer array controller component 518 includes circuitry configured to control the transducer array 128 for ultrasound signal transmissions and/or receptions of reflected ultrasound echo signals. The transducer array controller component 518 may receive control and/or data signals for operating the transducer array 128 from the systems 134 via the Ethernet cable 140 and the wireless router 132. For example, the transducer array controller component 518 may be in communication with the control logic dies 206 shown in FIG. 2 and may send trigger signals to initiate ultrasound signal transmissions and/or ultrasound echo receptions. In some embodiments, the transducer array controller component 518 may further include circuitry implementing some of the operations of the control logic dies 206. In some embodiments, the transducer array controller component 518 may further include circuitry configured to perform beamforming by combining ultrasound echo signals or responses received from the transducer array 128 and providing the combined or beamformed signals to the signal processing component 514.

The image processing component 516 is coupled to the signal processing component 514. The image processing component 516 includes circuitry configured to perform image processing. The image processing component 516 may function as an accelerator or engine for processing complex, computationally intensive image processing algorithms. In an embodiment, the image processing component 516 may perform noise reduction and/or image enhancement. For example, the image processing component 516 can perform clutter suppression, where clutters or imaging artifacts can be identified and removed. Alternatively, the image processing component 516 can perform ringdown subtraction, where ringdown artifacts at a range close to an excitation source (e.g., the transducers 212) are identified and removed.

In an embodiment, the image processing component 516 can transform the conditioned echo signals into other domains for image analysis. For example, the image processing component 516 can apply a fast Fourier transform (FFT) on the conditioned echoed signals for analysis in the frequency or spectral domain. For example, the image processing component 516 can identify a border line or a wall of a vessel (e.g., the vessel 120) and superimpose the border on a cross-sectional view of the vessel.

In an embodiment, the image processing component 516 may generate Doppler data by processing the conditioned echo signals into Doppler power or velocity information. The image processing component 516 may also generate B-mode data by applying envelope detection and logarithmic compression on the conditioned echo signals. The image processing component 516 can further generate images in various views, such as 2D and/or 3D views, based on the Doppler data or the B-mode data. The image processing component 516 can also perform various analyses and/or assessments. For example, the image processing component 516 can apply virtual histology (VH) techniques, for example, to analyze or assess plaques within a vessel (e.g., the vessel 120). The images can be generated to display a reconstructed color-coded tissue map of plaque composition superimposed on a cross-sectional view of the vessel.

In an embodiment, the image processing component 516 can apply a blood flow detection algorithm (e.g., ChromaFlo) to determine the movement of blood flow, for example, by acquiring image data of a target region (e.g., the vessel 120) repeatedly and determining the movement of the blood flow from the image data. The blood flow detection algorithm operates based on the principle that signals measured from vascular tissue are relatively static from acquisition to acquisition, whereas signals measured from blood flow vary at a characteristic rate corresponding to the flow rate. As such, the blood flow detection algorithm may determine movements of blood flow based on variations in signals measured from the target region between repeated acquisitions. To acquire the image data repeatedly, the transducer array controller component 518 can configure the transducer array 128 to transmit repeated pulses on the same aperture.

In an embodiment, the image processing component 516 can apply a border detection algorithm to automatically detect intraluminal vessel wall from the collected image signals by optimizing signals from the vascular tissue and characterize features of the intraluminal vessel wall.

The microcontroller 412 is coupled to the FPGA 414. For example, a control firmware may be stored on the memory 440 and executed by the microcontroller 412. The control firmware may include state machines 510 configured to control the operations of the FPGA 414. For example, the state machines 510 may control the starting and ending of a particular signal processing and/or image processing circuitry. While the microcontroller 412 is illustrated as a separate component from the FPGA 414, in some embodiments, the microcontroller 412 can be implemented as part of the FPGA 414.

The application processing component 416 is coupled to the FPGA 414. The application processing component 416 can include hardware and/or software. In some embodiments, the application processing component 416 may include a general purpose processor, a digital signal processor, and/or an application-specific integrated circuit (ASIC). The application processing component 416 is configured to generate image data from the conditioned echo signals. The application processing component 416 includes an image processing component 520 and an image formatting component 522. The image processing component 520 may implement image processing algorithms that are less computational intensive and/or require more flexibility or programmability compared to the image processing algorithms performed at the image processing component 516. For example, the image processing component 520 may perform contrast enhancement. Contrast enhancement changes the histogram of an image, for example, by representing areas of a target region of interest with more intensity levels and representing areas of the target region of less interest with less intensity levels. The change in the histogram may be achieved via a sigmoid-like curve, represented by a function $h:[0,1]\rightarrow[0,1]$. The curve may be configured to optimize image contrast for maximum clinical utility.

The image formatting component 522 is configured to format the image data according to image display formats suitable for display on the systems 134. For example, the image formatting component 522 can format the image data generated by the image processing components 516 and 520 according to a display frame rate and/or an available transmission bandwidth. The image formatting component 522 can also packetize the image data for transmission to the systems 134 via the wireless router 132. While the application processing component 416 is illustrated as a separate component from the FPGA 414, in some embodiments, the application processing component 416 can be implemented as part of the FPGA 414 and can be controlled by a firmware executing on the microcontroller 412 to provide flexibility. The image data generated by the image processing components 516 and 520 and/or formatted by the image formatting component 522 may be recorded and stored in the memory 440.

By implementing image processing and image formatting in the IVUS-PIM 130, the processed image data can be advantageously distributed in a format for display by any suitable display of the systems 134. In prior configurations, conditioned echo signals from a PIM would be transmitted to the particular computing device (e.g., a console) where the images would be generated. According to the present disclose, the image data are generated at the IVUS-PIM 130 without being transmitted to a particular system, and the image data can be transmitted in a display format to any number of systems 134. For example, image processing and image formatting can be completed entirely within the PIM 130 and the data for display can be transmitted from the PIM to any suitable computer/monitor for display. In this manner, the image processing and image formatting can be decoupled from larger, bulky computer systems and completed within relatively smaller, lighter, and more mobile PIM 130.

In some embodiments, the IVUS-PIM 130 may receive a control signal carrying control commands, such as start, stop, and/or record, for example, from IVUS control system 134b, and the processing component 410 may control the ultrasound imaging assembly 110 and/or image generations accordingly. In some embodiments, the IVUS-PIM 130 may receive a data signal indicating a border of an image, for example, from the medical diagnostic system 134a, and the processing component 410 may generate or re-compute the image data according to the received image border.

Figure 6:
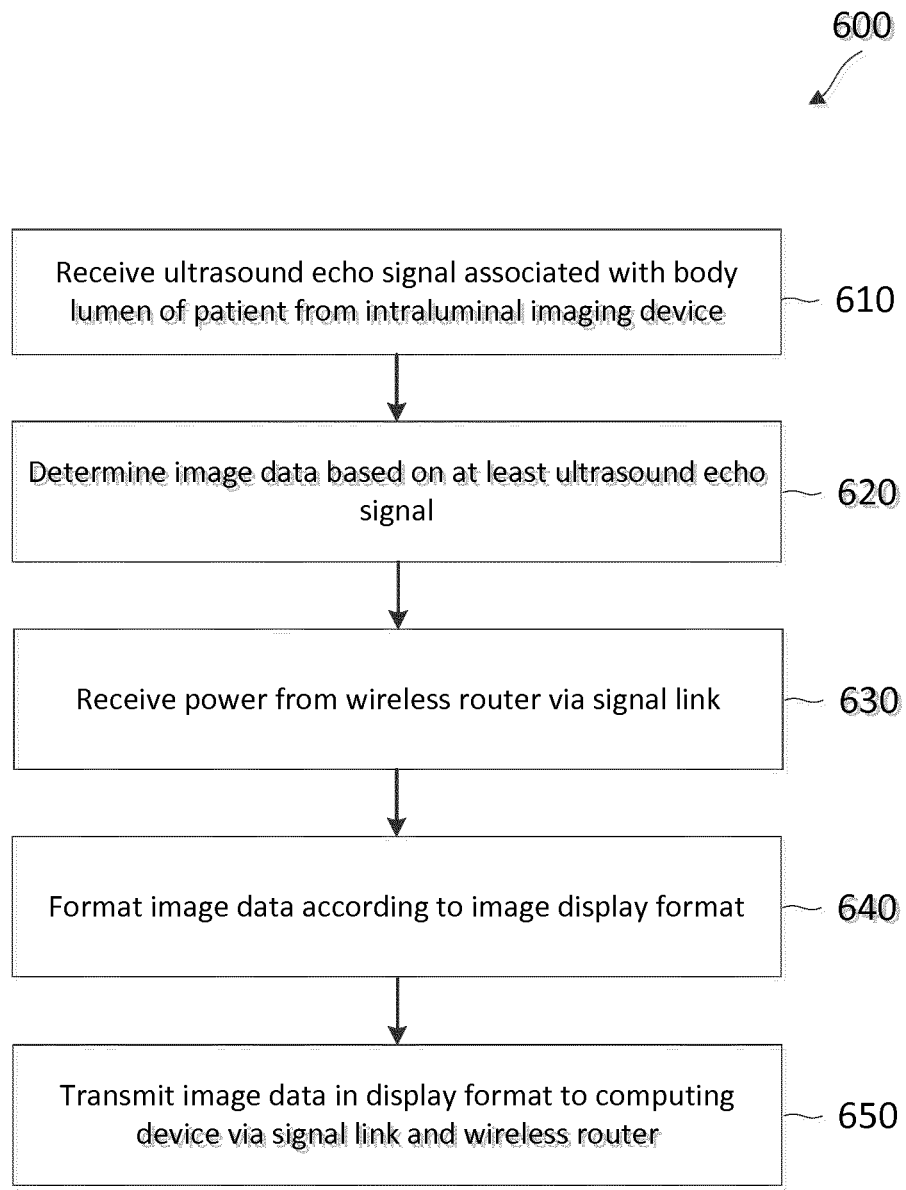
FIG. 6 is a flow diagram of a method of performing ultrasound imaging, according to aspects of the present disclosure.

FIG. 6 is a flow diagram of a method 600 of performing ultrasound imaging, according to aspects of the present disclosure. Steps of the method 600 can be executed by a computing device (e.g., a processor, processing circuit, and/or other suitable component) of a PIM such as the IVUS-PIM 130. The method 600 may employ similar mechanisms as described with respect to FIGS. 3, 4, and 5. As illustrated, the method 600 includes a number of enumerated steps, but embodiments of the method 600 may include additional steps before, after, and in between the enumerated steps. In some embodiments, one or more of the enumerated steps may be omitted or performed in a different order.

At step 610, the method 600 includes receiving an ultrasound echo signal associated with a body lumen of a patient from an intraluminal imaging device (e.g., the IVUS device 102). Then ultrasound echo signal may correspond to an ultrasound signal emitted by a transducer array (e.g., the transducer array 128) and reflected by surrounding tissues of a vessel (e.g., the vessel 120).

At step 620, the method 600 includes determining image data (e.g., image frames of a cross-sectional area of the vessel or a volume of an anatomical structure) based on at least the ultrasound echo signal.

At step 630, the method 600 includes receiving power (e.g., the power signal shown by the arrow 142) from a wireless router (e.g., the wireless router 132) via a signal link (e.g., the Ethernet cable 140).

At step 640, the method 600 includes formatting the image data according to an image display format of a computing device (e.g., the systems 134).

At step 650, the method 600 includes transmitting the image data in the image display format to the computing device (e.g., the systems 134) via the signal link and the wireless router.

Aspects of the present disclosure may provide several benefits. For example, the use of the PoE link for both power and data communications can reduce the amount of cabling that is typically required in an intraluminal system. The coupling of the PoE link to a wireless router enables the distribution of image data to multiple systems without additional cable connections. In addition, computing the image data at the IVUS-PIM can offload image processing and analytic algorithms that are typically computed at a target system with a direct wired connection to the IVUS device. Further, formatting the image data at the IVUS-PIM according to image display formats of the display systems allow the display systems to be light-weight, low-cost wireless devices and systems.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraluminal imaging system, comprising:
an intraluminal device comprising an ultrasound imaging component configured to be powered to obtain an ultrasound echo signal while the intraluminal device is positioned within a body lumen of a patient;
a wireless router;
a computing device in wireless communication with the wireless router;
a patient interface module (PIM);
a first cable coupled to the wireless router and the PIM, wherein the first cable comprises a network cable; and
a second cable coupled to the PIM and the intraluminal device,
wherein the PIM comprises:
a single housing such that only the first cable, the single housing, and the second cable are communicatively positioned between the wireless router and the intraluminal device;
a power-over-network component disposed within the single housing and different than the network cable, wherein the power-over-network component is configured to:
receive operating power from the wireless router at the PIM via the network cable;
provide at least a portion of the operating power from the PIM to the intraluminal device via the second cable such that the ultrasound imaging component is powered to obtain the ultrasound echo signal; and
at least one of a field programmable gate array (FPGA) or a processor disposed within the single housing and configured to:
receive the ultrasound echo signal; and
determine ultrasound image data based on at least the ultrasound echo signal,
wherein the power-over-network component is further configured to:
transmit the ultrasound image data to the computing device via the network cable and the wireless router such that data communication for the ultrasound image data is provided via the network cable.

2. The intraluminal imaging system of claim 1,
wherein the power-over-network component is further configured to receive a control signal from the computing device via the network cable and the wireless router, and
wherein the at least one of the FPGA or the processor is further configured to receive the ultrasound echo signal based on at least the control signal.

3. The intraluminal imaging system of claim 1,
wherein the power-over-network component is further configured to receive a control signal from the computing device via the network cable and the wireless router,
wherein the at least one of the FPGA or the processor is further configured to transmit an ultrasound signal transmission trigger to the ultrasound imaging component based on at least the control signal, and
wherein the ultrasound echo signal is associated with the ultrasound signal transmission trigger.

4. The intraluminal imaging system of claim 1,
wherein the power-over-network component is further configured to receive a control signal from the computing device via the network cable and the wireless router, and
wherein the at least one of the FPGA or the processor is further configured to determine the ultrasound image data based on the control signal.

5. The intraluminal imaging system of claim 1, wherein the PIM further includes a memory coupled to the at least one of the FPGA or the processor and configured to store the ultrasound image data.

6. The intraluminal imaging system of claim 1,
wherein the power-over-network component is further configured to receive, from a medical diagnostic system via the network cable and the wireless router, an image border line, and
wherein the at least one of the FPGA or the processor is further configured to determine the ultrasound image data further according to the image border line.

7. The intraluminal imaging system of claim 1, wherein the ultrasound imaging component comprises one or more ultrasound transducers.

8. The intraluminal imaging system of claim 1, wherein the PIM further comprises a patient isolation circuit coupled between the power-over-network component and the at least one of the FPGA or the processor.

9. The intraluminal imaging system of claim 1,
wherein the at least one of the FPGA or the processor is further configured to format the ultrasound image data according to an image display format usable by the computing device to display the ultrasound image data, and
wherein the power-over-network component is further configured to transmit the ultrasound image data by transmitting the ultrasound image data in the image display format usable by the computing device to display the ultrasound image data.

10. The intraluminal imaging system of claim 1,
wherein the PIM is in communication with a second computing device in wireless communication with the wireless router, and
wherein the power-over-network component is further configured to transmit, to the second computing device via the network cable and the wireless router, the ultrasound image data.

11. The intraluminal imaging system of claim 1,
wherein the power-over-network component comprises a direct current (DC)/DC converter,
wherein the power-over-network component is configured to:
convert, via the DC/DC converter, at least the portion of the operating power into a voltage level suitable for the intraluminal device; and
provide at least the portion of the operating power to the intraluminal device at the voltage level suitable for the intraluminal device.

12. The intraluminal imaging system of claim 11,
wherein the voltage level suitable for the intraluminal device comprises a voltage level suitable for the ultrasound imaging component, and
wherein, to provide at least the portion of the operating power to the intraluminal device at the voltage level suitable for the intraluminal device, the power-over-network component is configured to:

provide at least the portion of the operating power to the ultrasound imaging component at the voltage level suitable for the ultrasound imaging component.

13. The intraluminal imaging system of claim 11, wherein the power-over-network component is further configured to:
convert, via the DC/DC converter, at least a portion of the operating power received from the network cable into a voltage level suitable for the at least one of the FPGA or the processor; and
provide at least the portion of the operating power to the at least one of the FPGA or the processor at the voltage level suitable for the at least one of the FPGA or the processor.

14. The intraluminal imaging system of claim 1,
wherein the PIM comprises the FPGA;
wherein the PIM further comprises a microcontroller coupled to the FPGA and configured to execute control firmware to control operations of the FPGA,
wherein the ultrasound echo signal comprises an analog ultrasound echo signal, and
wherein the FPGA is configured to:
receive the analog ultrasound echo signal from the ultrasound imaging component;
perform an analog to digital conversion on the analog ultrasound echo signal to convert the analog ultrasound echo signal into a digital ultrasound echo signal;
perform signal conditioning on the digital ultrasound echo signal;
perform first image processing of the digital ultrasound echo signal after the signal conditioning; and
control the ultrasound imaging component to obtain the ultrasound echo signal.

15. The intraluminal imaging system of claim 14,
wherein the PIM comprises the processor distinct from the FPGA,
wherein the processor is configured to:
perform second image processing of the conditioned and first image processed digital ultrasound echo signal to produce the ultrasound image data; and
format the ultrasound image data according to an image display format usable by the computing device to display the ultrasound image data.

16. A method of performing intraluminal imaging, comprising:
receiving, by at least one of a field programmable gate array (FPGA) or a processor disposed within a single housing of a patient interface module (PIM), an ultrasound echo signal from an intraluminal imaging device comprising an ultrasound imaging component that is powered to obtain the ultrasound echo signal while the intraluminal imaging device is positioned within a body lumen of a patient;
determining, by the at least one of the field programmable gate array (FPGA) or the processor, ultrasound image data based on at least the ultrasound echo signal;
receiving, by a power-over-network component disposed within the single housing of the PIM, operating power from a wireless router at the PIM via a first cable coupled to the wireless router and the PIM, wherein the first cable comprises a network cable, wherein the power-over-network component is different than the network cable;
providing, by the power-over-network component, at least a portion of the operating power from the PIM to the intraluminal imaging device via a second cable such that the ultrasound imaging component is powered to obtain the ultrasound echo signal, wherein the second cable is coupled to the PIM and the intraluminal imaging device; and
transmitting, by the power-over-network component to a computing device via the network cable and the wireless router, the ultrasound image data such that data communication for the ultrasound image data is provided via the network cable,
wherein only the first cable, the single housing, and the second cable are communicatively positioned between the wireless router and the intraluminal device.

17. The method of claim 16, further comprising receiving, by the power-over-network component from the computing device via the network cable and the wireless router, a control signal, wherein the receiving the ultrasound echo signal includes receiving the ultrasound echo signal based on at least the control signal.

18. The method of claim 16, further comprising:
receiving, by the power-over-network component from the computing device via the network cable and the wireless router, a control signal; and
transmitting, by the at least one of the FPGA or the processor to the intraluminal imaging device, an ultrasound signal transmission trigger based on at least the control signal,
wherein the ultrasound echo signal is associated with the ultrasound signal transmission trigger.

19. The method of claim 16, further comprising receiving, by the power-over-network component from the computing device via the network cable and the wireless router, a control signal, wherein the determining the ultrasound image data includes determining the ultrasound image data further based on at least the control signal.

20. The method of claim 16, further comprising receiving, by the power-over-network component from a medical diagnostic system via the network cable and the wireless router, an image border line, wherein the determining the ultrasound image data includes determining the ultrasound image data according to the image border line.

21. The method of claim 16, further comprising formatting, by the at least one of the FPGA or the processor, the ultrasound image data according to an image display format of the computing device, wherein the transmitting the ultrasound image data includes transmitting the ultrasound image data in the image display format of the computing device.

22. The method of claim 16, further comprising transmitting, by the power-over-network component to a second computing device via the network cable and the wireless router, the ultrasound image data.

23. An intravascular imaging system, comprising:
an intravascular device comprising a medical sensor configured to be powered to obtain an intravascular imaging signal while the intravascular device is positioned within a blood vessel of a patient;
a wireless router;
a computing device in wireless communication with the wireless router;
a patient interface module (PIM);
a first cable coupled to the wireless router and the PIM, wherein the first cable comprises a network cable; and
a second cable coupled to the PIM and the intravascular device,
wherein the PIM comprises:
a single housing such that only the first cable, the single housing, and the second cable are communicatively positioned between the wireless router and the intravascular device;

a power-over-network component disposed within the single housing and different than the network cable, wherein the power-over-network component is configured to:
  receive operating power from the wireless router at the PIM via the network cable;
  provide at least a portion of the operating power from the PIM to the intravascular device via the second cable such that the medical sensor is powered to obtain the intravascular imaging signal; and
at least one of a field programmable gate array (FPGA) or a processor disposed within the single housing and configured to:
  receive the intravascular imaging signal; and
  determine intravascular image data based on at least the intravascular imaging signal,
wherein the power-over-network component is further configured to:
  transmit the intravascular image data to the computing device via the network cable and the wireless router such that data communication for the intravascular image data is provided via the network cable.

* * * * *